(12) United States Patent
Knerr

(10) Patent No.: US 8,399,741 B2
(45) Date of Patent: *Mar. 19, 2013

(54) MELON HAVING HIGH PERCENT SOLUBLE SOLIDS AND IMPROVED FIRMNESS

(75) Inventor: Larry D. Knerr, Hollister, CA (US)

(73) Assignee: Shamrock Seed Company, Inc., Salinas, CA (US)

( * ) Notice: Subject to any disclaimer, the term of this patent is extended or adjusted under 35 U.S.C. 154(b) by 741 days.

This patent is subject to a terminal disclaimer.

(21) Appl. No.: 12/206,827

(22) Filed: Sep. 9, 2008

(65) Prior Publication Data

US 2009/0007291 A1 Jan. 1, 2009

Related U.S. Application Data

(63) Continuation-in-part of application No. 11/041,343, filed on Jan. 24, 2005, now Pat. No. 7,572,954.

(51) Int. Cl.
A01H 1/00 (2006.01)
A01H 1/04 (2006.01)

(52) U.S. Cl. ........ 800/309; 800/260; 800/265; 800/266; 800/268; 800/269; 800/274

(58) Field of Classification Search ................. 800/260, 800/265, 266, 268, 269, 274, 309; 435/410
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,763,755 A | 6/1998 | Carlone | |
| 5,777,196 A | 7/1998 | Hall | |
| 5,850,009 A | 12/1998 | Kevern | |
| 5,948,957 A | 9/1999 | Chapko et al. | |
| 5,969,212 A | 10/1999 | Getschman | |
| 6,198,022 B1 * | 3/2001 | De Both et al. | 800/280 |
| 7,572,954 B2 * | 8/2009 | Knerr | 800/309 |

OTHER PUBLICATIONS da Graca Barreiro et al. Fruits 56(1): 51-58, 2001.*
Schultheis et al. Trends in new crops and new uses. 2002; pp. 439-444.*
Strang et al. Purdue Fruit and Vegetable Connection; Midwest Vegetable Variety Report for 2007; Bulletin B18246.*
Adelberg, J.W., et al., 1994. Explant origin affects the frequency of tetraploid plants from tissue culture of melon. HortScience 29(6):689-692.
Bennetzen, et al., 1992. Approaches and progress in the molecular cloning of plant disease resistance genes, in Genetic Engineering. 14:99-124, Ed. J.K. Setlow, Plenum Press, NY.
DeBolle, et al., 1996. Antimicrobial peptides from *Mirabilis jalapa* and *Amaranthus candatus*: expression, processing, localization and biological activity in transgenic tobacco. Plant Molec. Biol. 31:993-1008.
Ezura, et al., 1994. Ploidy of somatic embryos and the ability to regenerate plantlets in melons (*Cucumis melo* L.). Plant Cell Reports 14:107-111.
Kraft, et al., 2000. Linkage disequilibrium and fingerprinting in sugar beet. Theor. Appl. Genet. 101:323-326.
Pang, et al., 1992. Expression of a gene encoding a scorpion insectotoxin peptide in yeast, bacteria and plants. Gene 116:165-172.
Poehlman, J.M. and Sleper, D.A. Breeding Field Crops, 4$^{th}$ Ed. (1995), Iowa State University Press, Ames, Iowa, p. 473.
Zhang, et al., 1996. Development of genic male-sterile watermelon lines with delayed-green seedling marker. HortScience 31(1):123-126.

* cited by examiner

Primary Examiner — Kathleen K Bragdon
Assistant Examiner — Keith Robinson
(74) Attorney, Agent, or Firm — Jondle Plan Sciences Division Swanson & Bratschun, L.L.C.

(57) ABSTRACT

Honeydew melon having high percent soluble solids and improved firmness is disclosed. The invention relates to the seeds of honeydew melons SSC 112, SSC 135, SSC 118, 10217-3, 10233-1, 11466, 10888, 10288-1, and 11876-1, to the plants of honeydew melons SSC 112, SSC 135, SSC 118, 10217-3, 10233-1, 11466, 10888, 10288-1, and 11876-1, and to methods for producing a honeydew melon plant, either inbred or hybrid, by crossing each of the melons SSC 112, SSC 135, SSC 118, 10217-3, 10233-1, 11466, 10888, 10288-1, and 11876-1 with itself or another honeydew melon cultivar. The invention further relates to methods for producing a honeydew melon plant containing in its genetic material one or more transgenes and to the transgenic plants produced by that method and to methods for producing other honeydew melon cultivars derived from the melons SSC 112, SSC 135, SSC 118, 10217-3, 10233-1, 11466, 10888, 10288-1, and 11876-1.

13 Claims, No Drawings

MELON HAVING HIGH PERCENT SOLUBLE SOLIDS AND IMPROVED FIRMNESS

This application is a continuation-in-part application of prior application Ser. No. 11/041,343, filed Jan. 24, 2005 now U.S. Pat. No. 7,572,954 hereby incorporated by reference in its entirety.

BACKGROUND OF THE INVENTION

The present invention relates to new and distinctive honeydew melons (*Cucumis melo*) having high percent soluble solids and improved firmness. The invention further relates to honeydew melon hybrids SSC 112, SSC 135 and SSC 118, and inbreds 10217-3, 10233-1, 11466, 10888, 10288-1 and 11876-1. All publications cited in this application are herein incorporated by reference.

There are numerous steps in the development of any new, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as sugar levels, small cavity size, flesh color or texture, rind thinness, resistance to diseases and insects, and tolerance to drought and heat.

Practically speaking, all cultivated forms of honeydew melon belong to the highly polymorphic species *Cucumis melo* L. that is grown for its edible fruit. As a crop, honeydew melons are gown commercially wherever environmental conditions permit the production of an economically viable yield. Honeydew melon production and consumption have been increasing in the United States since 1993. Leading producers of fresh market honeydew melons in the U.S. are California, Arizona and Texas (1997 figures). The total U.S. crop of honeydew melons was produced on 29,400 acres, with a total yield of 5,795,000 cwt (average yield=197 cwt/acre), and a total value of $109,394,000 in 1997.

The honeydew melon is one of the most popular melons, belonging to the Inodorus group of *C. melo* that also includes the casaba melon. Of course, the best known member of the winter melon group is honeydew melon. Honeydew is an American name for the French variety 'White Antibes,' which was grown for many years in southern France and Algeria for foreign shipment. While the honeydew melon plant is similar to the casaba melon, except for more lobing of the leaf, the fruits are distinctive. They are round to slightly oval, about 8 inches long, and are fairly smooth, depending on the variety, with no netting or ribs. Some soft hairs are present on the surface in early stages; these hairs disappear when the fruit is ripe. Rind color is greenish white when immature, becoming somewhat creamy yellow when ripe. The flesh is light green, thick, juicy, sweet, and uniquely flavored. Newer varieties include orange fleshed honeydews.

*Cucumis melo* is a member of family Cucurbitaceae. The Cucurbitaceae is a family of about 90 genera and 700 to 760 species. The family includes pumpkins, squashes, gourds, watermelon, loofah and several weeds. The genus *Cucumis*, to which honeydew belongs, includes about 70 species. *Cucumis melo* includes a wide range of cultivated plants. Although crosses outside the species are sterile, intraspecific crosses are generally fertile, resulting in a wide range of variation. The more common cultivated plants fall into four main groups. First are the true cantaloupes of Europe. These have thick, scaly, rough, often deeply grooved, but not netted rinds. Second are the muskmelons, mostly grown in the United States, where they are called cantaloupes. These have finely netted rinds with shallow ribs. Third are the casaba or winter melons with large fruits. These have smooth, often yellow rinds. The honeydew melons are in this third group. Fourth are a group of elongated melons of India, China and Japan which are grown as vegetables.

Honeydew melon is a simple diploid species with twelve pairs of highly differentiated chromosomes. Large field spaces are required for honeydew melon and there is a need for labor-intensive hand-pollination for selfing as well as cross pollination. Honeydew melon flowers open after sunrise; the exact time depends on environmental conditions such as sunlight, temperature and humidity. The flower closes permanently in the afternoon of the same day Almost all pollen is collected and transferred before noon. Typically flowers are staminate although some are also hermaphroditic. Although hermaphroditic flowers are self-fertile, they are incapable of performing self-pollination. Insects are required for pollination. The primary pollinators are bees, particularly honeybees.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.). Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of honeydew melon plant breeding is to develop new, unique and superior honeydew melon cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same honeydew melon traits.

Each year, the plant breeder selects the germplasm to advance to the next generation. This germplasm is grown under unique and different geographical, climatic and soil conditions and further selections are then made during and at the end of the growing season. The cultivars that are developed are unpredictable because the breeder's selection occurs in unique environments with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large amounts of research monies to develop superior new honeydew melon cultivars.

The development of new honeydew melon cultivars requires the development and selection of honeydew melon varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, honeydew melon breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Honeydew melon (*Glycine max* L. Merr.) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD and three classical markers and four isozyme loci. See also, Shoemaker, R. C., RFLP Map of Honeydew melon, p 299-309, in Phillips, R. L. and Vasil, I. K. (eds.) DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in honeydew melon with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The first genetic maps of melon made using molecular markers were published in 1996 (Baudracco et al., Theor. Appl. Genet. 93:57-64) and in 1997 (Wang et al., Theor. Appl. Genet. 95:791-797). At the time few horticultural traits had been placed for melon, but since then, Perin et al. (Cucurbitaceae 1998:370-376) have constructed a genetic map of melon with molecular markers (AFLP and SSR) and horticultural traits, including *Fusarium* wilt resistance (gene Fom-1 and Fom-2) *Aphis gssypii* resistance (gene Vat), melon necrotic spot virus resistance (gene nvs), five carpels (gene p), green flesh color (gene gf) and various fruit characters. These markers may be advantageously used for breeding through Marker Assisted Selection as described in Zheng et al., Theor. Appl. Genet. 99:453-463, where PCR-based CAPS (cleaved amplified polymorphic sequences) were used as markers linked to resistance/susceptibility for *Fusarium* wilt in melon. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation breeding is another method of introducing new traits into honeydew melon varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromouracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "*Principles of Cultivar Development*" by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., *Theor. Appl. Genet.*, 77:889-892, 1989.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Honeydew melon, *Cucumis melo*, is an important and valuable field crop. Thus, a continuing goal of honeydew melon plant breeders is to develop stable, high yielding honeydew melon cultivars that are agronomically sound. The reasons for this goal are obviously to maximize the amount of fruit produced on the land used as well as to improve the fruit agronomic qualities. To accomplish this goal, the honeydew melon breeder must select and develop honeydew melon plants that have traits that result in superior cultivars.

SUMMARY OF THE INVENTION

It is an aspect of the present invention to provide melons having both a percent soluble solids of between 14.7% and 17.2% and a flesh firmness of between 6.7 pound force and 10.7 pound force.

It is another aspect of the present invention to provide new honeydew melon plants having an average percent soluble solids of between 14.7% and 17.2% including 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2 and all fractions thereof.

It is another aspect of the present invention to provide new honeydew melon plants having an average flesh firmness of between 6.7 pound force and 10.7 pound force including 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7 and all fractions thereof.

It is another aspect of the present invention to provide new honeydew melon plants that can be used efficiently to produce parent lines and hybrids possessing desirable traits in combination with high percent soluble solids and improved firmness.

It is yet another aspect of the present invention to provide a method for producing a honeydew melon that has both high percent soluble solids and improved firmness.

In accordance with yet another aspect of the present invention there has been provided numerous honeydew melon hybrids and inbreds having both high percent soluble solids and improved firmness.

According to the invention, there are provided honeydew melon hybrids designated SSC 112, SSC 135 and SSC 118, and honeydew melon inbreds designated 10217-3, 10233-1, 11466, 10888, 10288-1 and 11876-1 which have both high percent soluble solids and improved firmness. This invention thus relates to the seeds of honeydew melon hybrids SSC 112, SSC 135 and SSC 118, and honeydew melon inbreds 10217-3, 10233-1, 11466, 10888, 10288-1 and 11876-1, to the plants and plant parts of honeydew melon hybrids SSC 112, SSC 135 and SSC 118, and honeydew melon inbreds 10217-3, 10233-1, 11466, 10888, 10288-1 and 11876-1, and to the methods for producing a honeydew melon plant produced by crossing each hybrid or inbred with itself or another honeydew melon cultivar, and to methods for producing a honeydew melon plant containing in its genetic material one or more transgenes and to the transgenic honeydew melon plants produced by that method. This invention also relates to methods for producing other honeydew melon cultivars derived from honeydew melon hybrids SSC 112, SSC 135 and SSC 118, and honeydew melon inbreds 10217-3, 10233-1, 11466, 10888, 10288-1 and 11876-1 and to the honeydew melon cultivars derived by the use of those methods.

The honeydew melon plant of the invention may further comprise, or have, a cytoplasmic factor or other factor that is capable of conferring male sterility. Parts of the honeydew melon plant of the present invention are also provided, such as, for example, pollen obtained from an inbred plant and an ovule of the inbred plant.

In another aspect, the present invention provides regenerable cells for use in tissue culture of honeydew melon hybrids SSC 112, SSC 135, and SSC 118 and honeydew melon inbreds 10217-3, 10233-1, 11466, 10888, 10288-1 and 11876-1. The tissue culture will preferably be capable of regenerating plants having the physiological and morphological characteristics of the foregoing inbred honeydew melon plant, and of regenerating plant having substantially the same genotype as the foregoing inbred honeydew melon plant. Preferably, the regenerable cells in such tissue cultures will be embryos, protoplasts, meristematic cells, callus, pollen, anthers, pistils, leaves, stems, petioles, roots, root tips, or flowers or the like. Still further, the present invention provides honeydew melon plants regenerated from the tissue culture of the invention.

Another aspect of the invention is to provide methods for producing other inbred honeydew melon plants derived from honeydew melon hybrids SSC 112, SSC 135 and SSC 118, and honeydew melon inbreds 10217-3, 10233-1, 11466, 10888, 10288-1 and 11876-1. Inbred honeydew melon cultivars derived by the use of those methods are also part of the invention.

The invention also relates to methods for producing a honeydew melon plant containing in its genetic material one or more transgenes and to the transgenic honeydew melon plant produced by that method.

In another aspect, the present invention provides for single gene converted plants of honeydew melon hybrids SSC 112, SSC 135 and SSC 118, and honeydew melon inbreds 10217-3, 10233-1, 11466, 10888, 10288-1 and 11876-1. The single transferred gene may preferable by a dominant or recessive allele. Preferably, the single transferred gene will confer such traits as male sterility, male fertility, improved harvest characteristics, enhanced nutritional quality, and enhanced sugar content. The single gene may be a naturally occurring honeydew melon gene or a transgene introduced through genetic engineering techniques.

The invention further provides methods for developing honeydew melon plants in a honeydew melon plant breeding program using plant breeding techniques including recurrent selection, backcrossing, pedigree breeding, restriction fragment length polymorphism enhanced selection, genetic marker enhanced selection and transformation. Therefore, seeds, honeydew melon plants and parts thereof produced by such breeding methods are also part of the invention.

In another aspect, the present invention provides a method of introducing a desired trait into honeydew melon hybrids SSC 112, SSC 135 and SSC 118, and honeydew melon inbreds 10217-3, 10233-1, 11466, 10888, 10288-1 and 11876-1 wherein the method comprises crossing a plant selected from the group consisting of honeydew melon hybrids SSC 112, SSC 135 and SSC 118, and honeydew melon inbreds 10217-3, 10233-1, 11466, 10888, 10288-1 and 11876-1 with a plant of another honeydew melon cultivar that comprises a desired trait to produce F1 progeny plants, wherein the desired trait is selected from the group consisting of male sterility, herbicide resistance, insect resistance, and resistance to bacterial disease, fungal disease or viral disease; selecting progeny plants that have the desired trait to produce selected progeny plants; crossing the selected progeny plants with the selected parent plants to produce backcross progeny plants; selecting for backcross progeny plants that have the desired trait and physiological and morphological characteristics of the selected honeydew melon hybrid or inbred to produce selected backcross progeny plants; and repeating these steps to produce selected first or higher backcross progeny plants that comprise the desired trait and all of the physiological and morphological characteristics of the selected honeydew melon hybrid or inbred. Included in this aspect of the invention is the plant produced by the method wherein the plant has the desired trait and all of the physiological and morphological characteristics of the selected honeydew melon hybrid or inbred.

In another aspect, the present invention provides a method of introducing a desired trait into a honeydew melon having high soluble solids and improved flesh firmness wherein the method comprises crossing a plant having high soluble solids and improved flesh firmness with a plant of another honeydew melon cultivar that comprises a desired trait to produce F1 progeny plants, wherein the desired trait is selected from the group consisting of male sterility, herbicide resistance, insect resistance, and resistance to bacterial disease, fungal disease or viral disease; selecting progeny plants that have the desired trait to produce selected progeny plants; crossing the selected progeny plants with the recurrent parent plant to produce backcross progeny plants; selecting for backcross progeny plants that have the desired trait and physiological and morphological characteristics of the selected honeydew melon hybrid or inbred to produce selected backcross progeny plants; and repeating these steps to produce selected first or higher backcross progeny plants that comprise the desired trait and all of the physiological and morphological characteristics of the selected honeydew melon hybrid or inbred. Included in this aspect of the invention is the plant produced by the method wherein the plant has the desired trait and all of the physiological and morphological characteristics of the selected honeydew melon hybrid or inbred.

Other aspects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DEFINITIONS

In the description and tables that follow, a number of terms are used. In order to provide a clear and consistent understanding of the specification and claims, including the scope to be given such terms, the following definitions are provided:

Abscission Zone.

"Abscission zone" is the zone of abscission or separation of the fruit from the peduncle at maturity (controlled by ethylene). The resulting zone (or scar) ranges in size, small being preferred over large-range small (<10 mm), medium (10-15 mm), large (15-20 mm), very large (>20 mm).

Allele.

"Allele" is any of one or more alternative forms of a gene, all of which alleles relates to one trait or characteristic. In a diploid cell or organism, the two alleles of a given gene occupy corresponding loci on a pair of homologous chromosomes.

Backcrossing.

"Backcrossing" means a process in which a breeder repeatedly crosses hybrid progeny back to one of the parents, for example, a first generation hybrid $F_1$ with one of the parental genotype of the $F_1$ hybrid.

Blossom Scar.

"Blossom scar" is the remnant scar from the stigmatic surface of the blossom. There is a very broad range in sizes, small is better. Range is small (<10 mm), medium (10-20 mm), large (20-40 mm) and very large (>40 mm).

Cavity.

"Cavity" means the center of the honeydew melon fruit containing seeds and maternal tissues.

Commercially Acceptable.

As used herein, "commercially acceptable" means a honeydew melon variety having an average yield of 1000 boxes per acre, or more, over at least 2 years.

Doradoria.

"Doradia" is a physiological vine disorder occurring in Northern and Central Mexico. It includes a yellowing of the plant followed by eventual vine wilt and collapse. It is not pathogenic. Varieties differ in their degree of susceptibility/tolerance to this.

Essentially all the Physiological and Morphological Characteristics.

A plant having "essentially all the physiological and morphological characteristics" means a plant having the physiological and morphological characteristics, except for the characteristics derived from the converted gene.

Firm Fruit Exterior.

The firmness of the fruit exterior is subjectively tested under field conditions for resistance of the fruit exterior against a given pressure. The range is soft, medium, firm and very firm.

Flesh Firmness.

As used herein, "flesh firmness" means the average firmness of the melon flesh and is measured in pound-force with a hand-held penetrometer using a flat cylindrical 7 mm diameter probe inserted to a depth of 7 mm at a point midway between the fruit rind and seed cavity.

Flesh Color.

"Flesh color" means the degree of intensity of green. The range is pale, medium, medium dark, and deep.

Fruit Size.

Honeydew melons are sized based on the number of fruit that fit into a 30 lb carton. The dimensions (length and width) of the carton are specified as 17"×15¼". The depth must be at least 6½" but no more than 7½". Sizes range from 3s to 9s with 5s and 6s being the most common sizes.

Honeydew Melon.

As used herein, "honeydew melon" means a member of *Cucumis melo* L., group inodorus, having smooth, non-netted, non-ridged, light green to cream-colored or light yellow skin with light green flesh.

Non-Netted Skin.

As used herein, "non-netted skin" means a honeydew melon with no reticulate markings (no netting) on the skin. Melons with reticulate markings on the skin look like they have been draped with netting. An example of a netted melon is a cantaloupe. The extent of the netting can be very light to heavy depending on the type of melon. Commercially acceptable honeydew melons do not have any netting on the skin.

Non-Ridged.

As used herein, "non-ridged" means a honeydew melon which lacks ridges or fissures in the skin or rind. That is, the skin is completely smooth. An example of a melon with a ridged skin is Casaba.

Number of Boxes Per Acre.

"Number of Boxes per Acre" means the number of standard western melon packing boxes than can be filled by the fruit harvested per acre.

Percent (%) Soluble Solids.

"Percent soluble solids" means the average percent of soluble solid material found in the fruit tissue, the vast majority of which consists of sugars. Soluble solids are estimated with a refractometer and measured as degrees Brix.

Quantitative Trait Loci (QTL).

"Quantitative trait loci" means genetic loci that control to some degree numerically representable traits that are usually continuously distributed.

Regeneration.

"Regeneration" means the development of a plant from cell or protoplast tissue culture.

Season Maturity.

"Maturity" is considered the date of the onset of harvest and is described as Very Early, Early, Mid Early, Main and Late.

Single Gene Converted.

"Single gene converted" or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering. Single gene converted also refers to plants which are developed through mutation, either naturally occurring or induced.

Yield.

"Yield" is defined as concentrated, semi concentrated or extended. Concentrated=Harvested quantity of fruit in x consecutive days of harvest. Semi concentrated=Harvested quantity of fruit in x+3-5 consecutive days. Extended=Harvested quantity of fruit in x+6-10 days. The harvest may also be defined according to the same criteria, i.e. concentrated, when the plant sets all its fruits in a short period of time; semi concentrated or extended, when the plant sets all its fruits and allows picking for a longer period of time.

DETAILED DESCRIPTION OF THE INVENTION

Prior to the instant invention, a honeydew melon has never been developed having both high percent soluble solids and improved firmness. These traits have not previously been combined in any commercial or wild type honeydew melon. Having both traits in one honeydew melon substantially expands the utility of the crop by providing the highly desirable high soluble solids and greater flesh firmness.

All crop species are grown for the purpose of harvesting some product of commercial significance. Enhancement of productivity or yield of that product is a major goal of most plant breeding programs. The highest priority in most honeydew melon development programs is improving taste and firmness. It is a difficult challenge to incorporate both high percent soluble solids and improved firmness into honeydew melon. The difficulty is increased by several orders of magnitude if a breeder attempts to combine the increased firmness with the high percent soluble solids into one honeydew melon. For a plant breeder to find a cultivar with sufficient merit (e.g. high yielding) to be increased and commercially distributed, it is necessary to make many crosses and grow thousands of experimental genotypes. The evaluation of so many genotypes is a huge task, and consumes an enormous amount of the plant breeder's time and budget. In some instances, it can take a decade or more from the time the original cross is made to the time when a commercially viable genotype is identified.

The effectiveness of selecting for genotypes with the traits of interest (e.g. high percent soluble solids, improved firmness) in a breeding program will depend upon: 1) the extent to which the variability in the traits of interest of individual plants in a population is the result of genetic factors and is thus transmitted to the progenies of the selected genotypes; and 2) how much the variability in the traits of interest (high percent soluble solids, improved firmness) among the plants is due to the environment in which the different genotypes are growing. The inheritance of traits ranges from control by one major gene whose expression is not influence by the environment (i.e., qualitative characters) to control by many genes whose effects are influenced by the environment (i.e., quantitative characters). Breeding for quantitative traits is further characterized by the fact that: 1) the differences resulting from the effect of each gene are small, making it difficult or impossible to identify them individually; 2) the number of genes contributing to a character is large, so that distinct segregation ratios are seldom if ever obtained; and 3) the effects of the genes may be expressed in different ways based on environmental variation. Therefore, the accurate identification of transgressive segregants or superior genotypes with the traits of interest is extremely difficult and its success is dependent on the plant breeder's ability to minimize the environmental variation affecting the expression of the quantitative character in the population. The likelihood of identifying a transgressive segregant is greatly reduced as the number of traits combined into one genotype is increased.

The methods used in cultivar development programs and their probability of success are dependent on the number of characters to be improved simultaneously, such as high percent soluble solids, improved firmness, yield, and disease resistance traits. The proportion of desired individuals for multiple characters in a population is obtained by multiplying together the proportion of desired individuals expected in the population for each character to be improved. This assumes that the characters are inherited independently, i.e., are not genetically linked.

These principles can be applied not only to traditionally bred lines, but to transgenic lines as well. Whether combining desirable traditional and transgenic traits via hybridization of transgenic lines or cotransformation of multiple genes into one line, the combined effects on yield are likely to be multiplicative. The likelihood of identifying a line with a suitable combination of traits is further reduced when considering the potential effects of a transgene on the regulation of metabolism within a plant.

It is an extremely difficult hurdle to combine improved firmness with a high percent soluble solids content in a given honeydew melon hybrid or inbred. Unexpectedly, the traits of high percent soluble solids and improved firmness have been combined in commercially acceptable honeydew melon hybrids and inbreds in the present invention. Once these traits have been combined in a variety, then the traits can be transferred to other genetic backgrounds.

EXAMPLES

The following examples are provided to further illustrate the present invention and are not intended to limit the invention beyond the limitations set forth in the appended claims.

Example 1

Honeydew melon hybrid SSC 112 having both high percent soluble solids and improved firmness. One example of high percent soluble solids and improved firmness is honeydew melon hybrid SSC 112. SSC 112 was developed through plant breeding and is stable and uniform. Some of the criteria used to select in various generations include: firmness, high percent soluble solids, and days to maturity.

Honeydew melon hybrid SSC 112 is an andromonoecious honeydew melon with superior characteristics. Honeydew melon hybrid SSC 112 is best adapted to southern and southwestern regions of the USA as well as Latin America. Honeydew melon hybrid SSC 112 produces attractive, round fruit with crisp flesh, heavy production 4s, 5s and a few 6s, small to medium seed cavity and a small blossom scar. The yield is very high, with an extended harvest profile. The level of soluble solids is very high. The vine is very vigorous with excellent fruit coverage and a very dark green color. Honeydew melon hybrid SSC 112 is tolerant to race 2 of Powdery Mildew (*Sphaerotheca fuliginea*) and also has tolerance to sulfur applications. Honeydew melon hybrid SSC 112 has a relative maturity of 86 days.

Honeydew melon hybrid SSC 112 has shown uniformity and stability for the traits, within the limits of environmental influence for the traits. The line has been increased with continued observation for uniformity. No variant traits have been observed or are expected in hybrid SSC 112.

Honeydew melon hybrid SSC 112 has the following morphologic and other characteristics as shown in Table 1. Column 1 shows the characteristic and column 2 shows the expression of that characteristic by melon hybrid SSC 112.

TABLE 1

| Characteristic | SSC 112 |
| --- | --- |
| Sex Expression | Andromonoecious |
| Growth | Indeterminate |
| Fruit Size | Mostly 4s and 5s with some 6s |
| Fruit shape | Round |
| Days to Maturity | 86 |
| Percent soluble solids | 14.69 |
| Fruit flesh firmness | 8.516 |
| Disease Reactions | Resistant to *Sphaerotheca fuliginea* (Powdery Mildew) Race 2 |
| Sulfur application reactions | Tolerant |

Example 2

A second example of high percent soluble solids and improved firmness is honeydew melon inbred 10217-3. Honeydew melon inbred 10217-3 is a parent of hybrid SSC 112 and has both high percent soluble solids and improved firmness. 10217-3 was developed through plant breeding and is stable and uniform. Some of the criteria used to select in various generations include: firmness, high percent soluble solids, and days to maturity.

10217-3 is an andromonoecious honeydew melon with superior characteristics, and provides an excellent parental line in crosses for producing first generation ($F_1$) hybrid honeydew melon. Honeydew melon inbred 10217-3 is best adapted to southern and southwestern regions of the USA as well as Latin America.

Honeydew melon inbred 10217-3 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 10217-3.

Honeydew melon inbred 10217-3 has the following morphologic and other characteristics as shown in Table 2. Column 1 shows the characteristic and column 2 shows the expression of that characteristic by melon inbred 10217-3.

TABLE 2

| Characteristic | 10217-3 |
|---|---|
| Sex Expression | Andromonoecious |
| Growth | Indeterminate |
| Fruit Size | Mostly 4s, some 5s |
| Fruit shape | Round |
| Days to Maturity | 90 |
| Percent soluble solids | 16.53 |
| Fruit flesh firmness | 6.733 |

Example 3

A third example of high percent soluble solids and improved firmness is honeydew melon inbred 10233-1. Honeydew melon inbred 10233-1 is a parent of hybrid SSC 112 and has both high percent soluble solids and improved firmness. 10233-1 was developed through plant breeding and is stable and uniform. Some of the criteria used to select in various generations include: firmness, high percent soluble solids, and days to maturity.

Honeydew melon inbred 10233-1 is an andromonoecious honeydew melon with superior characteristics, and provides an excellent parental line in crosses for producing first generation ($F_1$) hybrid honeydew melon. Honeydew melon inbred 10233-1 is best adapted to southern and southwestern regions of the USA as well as Latin America.

Honeydew melon inbred 10233-1 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 10233-1.

Honeydew melon inbred 10233-1 has the following morphologic and other characteristics as shown in Table 3. Column 1 shows the characteristic and column 2 shows the expression of that characteristic by melon inbred 10233-1.

TABLE 3

| Characteristic | 10233-1 |
|---|---|
| Sex Expression | Andromonoecious |
| Growth | Indeterminate |
| Fruit Size | Mostly 5s and 6s |
| Fruit shape | Round |
| Days to Maturity | 83 |
| Percent soluble solids | 13.81 |
| Fruit flesh firmness | 8.833 |

Example 4

A fourth example of high percent soluble solids and improved firmness is honeydew melon hybrid SSC 134. SSC 134 was developed through plant breeding and is stable and uniform. Some of the criteria used to select in various generations include: firmness, high percent soluble solids, and days to maturity.

Honeydew melon hybrid SSC 134 is an andromonoecious honeydew melon with superior characteristics. Honeydew melon hybrid SSC 134 is best adapted to southern and southwestern regions of the USA as well as Latin America.

The honeydew melon hybrid SSC 134 has shown uniformity and stability for the traits, within the limits of environmental influence for the traits. The line has been increased with continued observation for uniformity. No variant traits have been observed or are expected in hybrid SSC 134.

Honeydew melon hybrid SSC 134 has the following morphologic and other characteristics as shown in Table 4. Column 1 shows the characteristic and column 2 shows the expression of that characteristic by melon hybrid SSC 134.

TABLE 4

| Characteristic | SSC 134 |
|---|---|
| Sex Expression | Andromonoecious |
| Growth | Indeterminate |
| Fruit Size | Mostly 5s with some 4s and 6s |
| Fruit shape | Round, slightly oval |
| Days to Maturity | 85 |
| Percent soluble solids | 14.41 |
| Fruit flesh firmness | 8.438 |

Example 5

A fifth example of high percent soluble solids and improved firmness is honeydew melon inbred 11466. Honeydew melon inbred 11466 is a parent of both hybrid SSC 134 and hybrid SSC 135 and has both high percent soluble solids and improved firmness. 11466 was developed through plant breeding and is stable and uniform. Some of the criteria used to select in various generations include: firmness, high percent soluble solids, and days to maturity.

Honeydew melon inbred 11466 is an andromonoecious honeydew melon with superior characteristics, and provides an excellent parental line in crosses for producing first generation ($F_1$) hybrid honeydew melon. Honeydew melon inbred 11466 is best adapted to southern and southwestern regions of the USA as well as Latin America. It is a very firm, smooth honeydew with a very tight seed cavity.

The honeydew melon inbred 11466 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 11466.

Honeydew melon inbred 11466 has the following morphologic and other characteristics as shown in Table 5. Column 1 shows the characteristic and column 2 shows the expression of that characteristic by melon inbred 11466.

TABLE 5

| Characteristic | 11466 |
| --- | --- |
| Sex Expression | Andromonoecious |
| Growth | Indeterminate |
| Fruit Size | Mostly 5s with some 6s |
| Fruit shape | Round, slightly flattened |
| Days to Maturity | 90 |
| Percent soluble solids | 13.16 |
| Fruit flesh firmness | 9.913 |

Example 6

A sixth example of high percent soluble solids and improved firmness is honeydew melon inbred 11647. Honeydew melon inbred 11647 is a parent of SSC 134 and has both high percent soluble solids and improved firmness. 11647 was developed through plant breeding and is stable and uniform. Some of the criteria used to select in various generations include: firmness, high percent soluble solids, and days to maturity.

Honeydew melon inbred 11647 is an andromonoecious honeydew melon with superior characteristics, and provides an excellent parental line in crosses for producing first generation ($F_1$) hybrid honeydew melon. Honeydew melon inbred 11647 is best adapted to southern and southwestern regions of the USA as well as Latin America.

The honeydew melon inbred 11647 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 11647.

Honeydew melon inbred 11647 has the following morphologic and other characteristics as shown in Table 6. Column 1 shows the characteristic and column 2 shows the expression of that characteristic by melon inbred 11647.

TABLE 6

| Characteristic | 11647 |
| --- | --- |
| Sex Expression | Andromonoecious |
| Growth | Indeterminate |
| Fruit Size | Mostly 5s with some 4s |
| Fruit shape | Round, slightly oval |
| Days to Maturity | 91 |
| Percent soluble solids | 15.2 |
| Fruit flesh firmness | 4.850 |

Example 7

A seventh example of high percent soluble solids and improved firmness is honeydew melon hybrid SSC 135. SSC 135 was developed through plant breeding and is stable and uniform. Some of the criteria used to select in various generations include: firmness, high percent soluble solids, and days to maturity.

Honeydew melon hybrid SSC 135 is an andromonoecious honeydew melon with superior characteristics. Honeydew melon hybrid SSC 135 is best adapted to southern and southwestern regions of the USA as well as Latin America.

Honeydew melon hybrid SSC 135 has shown uniformity and stability for the traits, within the limits of environmental influence for the traits. The line has been increased with continued observation for uniformity. No variant traits have been observed or are expected in hybrid SSC 135.

Honeydew melon hybrid SSC 135 has the following morphologic and other characteristics as shown in Table 7. Column 1 shows the characteristic and column 2 shows the expression of that characteristic by melon hybrid SSC 135.

TABLE 7

| Characteristic | SSC 135 |
| --- | --- |
| Sex Expression | Andromonoecious |
| Growth | Indeterminate |
| Fruit Size | Mostly 4s and 5s |
| Fruit shape | Round, slightly oval |
| Days to Maturity | 81 |
| Percent soluble solids | 14.00 |
| Fruit flesh firmness | 9.00 |

Example 8

An eighth example of high percent soluble solids and improved firmness is honeydew melon inbred 11876-1. 11876-1 was developed through plant breeding and is stable and uniform. Some of the criteria used to select in various generations include: firmness, high percent soluble solids, and days to maturity.

Honeydew melon inbred 11876-1 is an andromonoecious honeydew melon with superior characteristics, and provides an excellent parental line in crosses for producing first generation ($F_1$) hybrid honeydew melon. Honeydew melon inbred 11876-1 is best adapted to southern and southwestern regions of the USA as well as Latin America.

The honeydew melon inbred 11876-1 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 11876-1.

Honeydew melon inbred 11876-1 has the following morphologic and other characteristics as shown in Table 8. Column 1 shows the characteristic and column 2 shows the expression of that characteristic by melon inbred 11876-1.

TABLE 8

| Characteristic | 11876-1 |
| --- | --- |
| Sex Expression | Andromonoecious |
| Growth | Indeterminate |
| Fruit Size | Mostly 4s and 5s |
| Fruit shape | Round, slightly flattened |
| Days to Maturity | 87 |
| Percent soluble solids | 13.08 |
| Fruit flesh firmness | 8.100 |

Example 9

A ninth example of high percent soluble solids and improved firmness is honeydew melon hybrid SSC 118. SSC 118 was developed through plant breeding and is stable and uniform. Some of the criteria used to select in various generations include: firmness, high percent soluble solids, and days to maturity.

Honeydew melon hybrid SSC 118 is an andromonoecious honeydew melon with superior characteristics. Honeydew melon hybrid SSC 118 is best adapted to southern and southwestern regions of the USA as well as Latin America.

Honeydew melon hybrid SSC 118 has shown uniformity and stability for the traits, within the limits of environmental influence for the traits. The line has been increased with continued observation for uniformity. No variant traits have been observed or are expected in hybrid SSC 118.

Honeydew melon hybrid SSC 118 has the following morphologic and other characteristics as shown in Table 9. Column 1 shows the characteristic and column 2 shows the expression of that characteristic by melon hybrid SSC 118.

TABLE 9

| Characteristic | SSC 118 |
| --- | --- |
| Sex Expression | Andromonoecious |
| Growth | Indeterminate |
| Fruit Size | Mostly 5s and 6s with some 4s |
| Fruit shape | Slightly oval |
| Days to Maturity | 81 |
| Percent soluble solids | 13.75 |
| Fruit flesh firmness | 5.506 |

Example 10

A tenth example of high percent soluble solids and improved firmness is honeydew melon inbred 10888. Honeydew melon inbred 10888 is a parent of SSC 118 and has both high percent soluble solids and improved firmness. 10888 was developed through plant breeding and is stable and uniform. Some of the criteria used to select in various generations include: firmness, high percent soluble solids, and days to maturity.

Honeydew melon inbred 10888 is an andromonoecious honeydew melon with superior characteristics, and provides an excellent parental line in crosses for producing first generation ($F_1$) hybrid honeydew melon. Honeydew melon inbred 10888 is best adapted to southern and southwestern regions of the USA as well as Latin America.

The honeydew melon inbred 10888 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 10888.

Honeydew melon inbred 10888 has the following morphologic and other characteristics as shown in Table 10. Column 1 shows the characteristic and column 2 shows the expression of that characteristic by melon inbred 10888.

TABLE 10

| Characteristic | 10888 |
| --- | --- |
| Sex Expression | Andromonoecious |
| Growth | Indeterminate |
| Fruit Size | Mostly 6s with some 5s |
| Fruit shape | Round |
| Days to Maturity | 86 |

TABLE 10-continued

| Characteristic | 10888 |
| --- | --- |
| Percent soluble solids | 15.18 |
| Fruit flesh firmness | 4.300 |

Example 11

An eleventh example of high percent soluble solids and improved firmness is honeydew melon inbred 10228-1. Honeydew melon 10228-1 is a parent of SSC 118 and has both high percent soluble solids and improved firmness. 10228-1 was developed through plant breeding and is stable and uniform. Some of the criteria used to select in various generations include: firmness, high percent soluble solids, and days to maturity.

Honeydew melon inbred 10228-1 is an andromonoecious honeydew melon with superior characteristics, and provides an excellent parental line in crosses for producing first generation ($F_1$) hybrid honeydew melon. Honeydew melon inbred 10228-1 is best adapted to southern and southwestern regions of the USA as well as Latin America.

The honeydew melon inbred 10228-1 has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 10228-1.

Honeydew melon inbred 10228-1 has the following morphologic and other characteristics as shown in Table 11. Column 1 shows the characteristic and column 2 shows the expression of that characteristic by melon inbred 10228-1.

TABLE 11

| Characteristic | 10228-1 |
| --- | --- |
| Sex Expression | Andromonoecious |
| Growth | Indeterminate |
| Fruit Size | Mostly 5s with some 6s |
| Fruit shape | Oval |
| Days to Maturity | 90 |
| Percent soluble solids | 12.56 |
| Fruit flesh firmness | 6.73 |

The present invention characteristics of high soluble solids of between 14.7% and 17.3% and improved firmness of between 6.7 and 10.7 have been transferred into numerous different honeydew melon genetic backgrounds, including 10217-3, 10233-1, SSC 112, 11466, 11647, SSC 134 SSC 135, 10888, SSC 118, and 11876-1. The data for percent soluble solids and flesh firmness for each of these 11 different genetic backgrounds are shown and described in the Specification in each of Tables 1-34.

Deposits of seed of each of the honeydew melon hybrids, SSC 112, SSC 135 and SSC 118, and honeydew melon inbreds, 10217-3, 10233-1, 11466, 10888, 10228-1 and 11876-1 will be made with the American Type Culture Collection (ATCC), Manassas, Va., USA. Using the deposited seed of any of the inbreds or hybrids, a skilled plant breeder can transfer the present invention characteristics of high percent soluble solids and improved flesh firmness into many other honeydew melon genetic backgrounds through breeding techniques well-known in the art, including backcross breeding.

Further Embodiments of the Invention

This invention also is directed to methods for producing a honeydew melon plant by crossing a first parent honeydew melon plant with a second parent honeydew melon plant wherein either the first or second parent honeydew melon plant is a honeydew melon plant selected from the group consisting of hybrids SSC 112, SSC 135 and SSC 118 and inbreds 10217-3, 10233-1, 11466, 10888, 10288-1 and 11876-1. Further, both first and second parent honeydew melon plants can come from any of the listed inbreds and hybrids. Still further, this invention also is directed to methods for producing a honeydew melon plant by crossing any of the listed honeydew melon inbreds or hybrids with a second honeydew melon plant and growing the progeny seed, and repeating the crossing and growing steps with the selected honeydew melon inbred or hybrid-derived plant from 0 to 7 times. Thus, any such methods using any of the listed honeydew melon inbreds or hybrids are part of this invention: selfing, backcrosses, hybrid production, crosses to populations, and the like. All plants produced using any of the listed honeydew melon inbreds or hybrids as a parent are within the scope of this invention, including plants derived from any of the listed honeydew melon inbreds or hybrids. Advantageously, the honeydew melon inbreds and hybrids are used in crosses with other, different, honeydew melon cultivars to produce first generation ($F_1$) honeydew melon hybrid seeds and plants with superior characteristics.

It should be understood that these inbreds and hybrids can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which honeydew melon plants can be regenerated, plant calli, plant clumps and plant cells that are intact in plants or parts of plants, such as embryos, pollen, ovules, flowers, leaves, stalks, and the like.

As it is well known in the art, tissue culture of honeydew melon can be used for the in vitro regeneration of honeydew melon plants. Tissues cultures of various tissues of honeydew melon and regeneration of plants therefrom are well known and published. By way of example, a tissue culture comprising organs has been used to produce regenerated plants as described in Dirks R., et al. *Plant Cell Report* 7: 8 626-627 (1989); Tahar, S. B., et al. *Cucurbit Genetics Cooperative Reports* 12:21-27 (1989); Homma, Y., et al. *Japan J. Breed* 41:543-551 (1991).Yoshioka, K., et al. *Japan J Breed* 42:277-285 (1992); Debeaujon, I., et al. *Pl Cell Rep* 12:37-40 (1992); Tabei, Y., et al. *J Jap Soc Hort Sci* 61:317-322 (1992); Debeaujon, I., et al. *Plant Cell Tissue Org Cult* 34:91-100 (1993); Fang, G. W., et al. *Molecular Plant—Microbe Interactions* 6:358-367 (1993); Valles, M. P., et al. *Pl Cell Rep* 13:145-148 (1994); Ezura, H., et al. *Pl Cell Rep* 14:107-111 (1994); Ezura, H., et al. *Pl Cell Rep* 14:684-688 (1995); Kathal, R., et al. *Plant Sci* 96:137-142 (1994); Adelberg, J. W., et al. *Hortscience* 29:689-692 (1994). More precisely, in the case of melons (*C. melo*), regeneration through organogenesis has been described either directly on cotyledons placed in culture (Smith, S. et al., *Abstract Proc. Annual TCA Meeting*, Las Vegas, Nev., (1988), Dirks, R. et al., *Plant Cell Reports*, 7:626-627 (1989)), or through the intermediary of calli derived from cotyledons (Mackay, W. et al., *Cucurbit Genetics Cooperative*, 11:33-34 (1988), Moreno, V. et al., *Plant Cell Tissue and Organ Culture*, 5:139-146 (1985), Orts, M. et al., *Hort Science*, 22:666 (1987), Bouabdalla, L. et al., *Z. Pflanzenz chtung*, 96:82-85 (1986)), hypocotyls (Abak, K. et al., *Cucurbit Genetics Cooperative Report*, 3:27-29 (1980), Kathal, R. et al., *J. Plant Physiol.*, 126:59-62 (1986)) or leaves (Kathal, R. et al., *Plant Cell Report*, 7:449-451 (1988)). The production of melon plants derived from somatic embryos has also been reported (Oridate, T. et al., *Japan J. Breeding*, 36:424-428 (1986), Branchard, M. et al., *C.R. Acad. Sci.* Paris, 307, Serie III:777-780 (1988)). Also, De Both et al. in U.S. Pat. No. 6,198,022 teach how to regenerate plants having a normal phenotype from cotyledons. It is clear from the literature that the state of the art is such that these methods of obtaining plants are conventional in the sense that they are routinely used and have a very high rate of success. Thus, another aspect of this invention is to provide cells which upon growth and differentiation produce honeydew melon plants having the physiological and morphological characteristics of the honeydew melon inbred or hybrid selected from the above list.

With the advent of molecular biological techniques that have allowed the isolation and characterization of genes that encode specific protein products, scientists in the field of plant biology have developed a strong interest in engineering the genome of plants to contain and express foreign genes, or additional, or modified versions of native, or endogenous, genes (perhaps driven by different promoters) in order to alter the traits of a plant in a specific manner Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed honeydew melon plants, using transformation methods as described below to incorporate transgenes into the genetic material of the honeydew melon plant(s).

Expression Vectors for Honeydew Melon Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. USA*, 80:4803 (1983), Valles et al., *Plant Cell Report*, 13:3-4 145-148 (1994), Fang et al., *Plant Cell Report*, 9:3 160-164 (1990). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985); Gordon-Kamm et al., *Plant Cell* 2:603-618 (1990); Stalker et al., *Science* 242: 419-423 (1988) and Qui Zhijun et al., *International Journal of Horticultural Science* 5:3/4 46-49 (1999).

Other selectable marker genes for plant transformation not of bacterial origin include, for example, mouse dihydrofolate reductase, plant 5-enolpyruvyl-shikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include Beta-glucuronidase (GUS), alpha-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Valles et al, *Plant Cell Report* 3:3-4 145-148 (1994), Shetty et al., *FoodBiotechnology* 11:2 111-128 (1997).

In vivo methods for visualizing GUS activity that do not require destruction of plant tissue are available. Molecular Probes publication 2908, Imagene Green™, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers. A gene encoding Green Fluorescent Protein (GFP) has also been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in honeydew melon. Optionally, the inducible promoter is operably linked to a nucleotide sequence encoding a signal sequence which is operably linked to a gene for expression in honeydew melon. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) Tet repressor from Tn10 (Gatz et al., *Mol. Gen. Genetics* 227:229-237 (1991)) or the salicylic acid inducible promoter region of the protein gene PR1 from tobacco (Shetty et al., *FoodBiotechnology* 11:2 111-128 (1997)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters

A constitutive promoter is operably linked to a gene for expression in honeydew melon or the constitutive promoter is operably linked to a nucleotide sequence encoding a signal sequence which is operably linked to a gene for expression in honeydew melon.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985), Dong et al., Biotechnology 9:9 858-863 (1991)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT application WO96/30530.

C. Tissue-Specific or Tissue-Preferred Promoters

A tissue-specific promoter is operably linked to a gene for expression in honeydew melon. Optionally, the tissue-specific promoter is operably linked to a nucleotide sequence encoding a signal sequence which is operably linked to a gene for expression in honeydew melon. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); and Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is honeydew melon. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A gene coding for the coat protein of the cucumber mosaic virus (CMV), see Gonzalves et al., *Journal of the American Society for Horticultural Science.* 1994, 119: 2, 345-355.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

S. A gene of the Zucchini Yellow Mosaic Potyvirus (ZYMV) coat protein that, when introduced into melon by *Agrobacterium tumefaciens*-mediated transformation, seems to render the transformed melon immune to infection by ZYMV. See for example Fang et al., *Molecular Plant Microbe Interaction*. 1993, 6: 3, 358-367.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvyl-3-shikimate-phospho-synthase (EPSP) and aroA genes, respectively) and other phosphono compounds such as glufosinate (phosphinothricin acetyl transferase (PAT) and *Streptomyces hygroscopicus* phosphinothricin-acetyl transferase, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for PAT activity. Exemplary of genes conferring resistance to phenoxy propionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Increased sweetness and flavor of the fruit by introduction of a gene encoding sweet tasting proteins such as monellin (Penarrubia et al., *Bio/Technology*. 1992, 10: 5, 561-564) or thaumatin (Szwack et al., *Proceedings of the IXth International Congress of the International Association of Plant Tissue Culture and Biotechnology*, Jerusalem, Israel, 14-19 Jun. 1998).

B. Reduced ethylene biosynthesis to control ripening by introduction of an antisense construct of ACC oxidase into *Cucumis melo*. For example, see Guis et al., *Proceedings if*

*the eighth International Symposium on Plant Bioregulators in Fruit Production*, Val. Spain, 1-4 Apr. 1997.

C. Improved salt tolerance by transforming *Cucumis melo* plants with HAL 1, a yeast regulatory gene involved in stress tolerance, as shown in Serrano et al., *Scientia Horticulturae.* 1999, 78: 1/4, 261-269 and in Bordas et al., *Transgenic Research.* 1997, 6: 1, 41-50.

D. Male sterile plants, especially useful in hybrid melon production, by introduction of a gene encoding a tobacco PR Glucanase as described in (WO9738116) that can also be used in melon.

Methods for Honeydew Melon Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227:1229 (1985). Guis et al., *Scientia Horticulturae.* 2000, 84:1/2, 91-99, Ann et al., *Embo J.* 277-284:4, (1985), Jefferson et al., *Embo J.* 3901-390764, (1987), Valles et al., *Pl Cell. Rep.* 145-148:13 (1984). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 6,198,022 issued Mar. 6, 2001.

B. Direct Gene Transfer

Despite the fact the host range for *Agrobacterium*-mediated transformation is broad, some major cereal crop or vegetable species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation collectively referred to as direct gene transfer have been developed as an alternative to *Agrobacterium*-mediated transformation.

A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992), Gonzalves et al., *Journal of the American Society for Horticultural Science.* 1994, 119: 2, 345-355, Gray et al., *Plant Cell Tissue and Organ Culture.* 1994, 37:2, 179-184.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992), Spencer et al., *Plant Mol. Biol.* 24:51-61 (1994) and Nishigushi et al., *Bulletin of the National Institute of Agrobiological Resources Japan.* 1988, 4, 177-187.

Following transformation of honeydew melon target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular honeydew melon line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term honeydew melon plant is used in the context of the present invention, this also includes any single gene conversions of that cultivar. The term single gene converted plant as used herein refers to those honeydew melon plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental honeydew melon plants for that cultivar. The parental honeydew melon plant which contributes the gene for the desired characteristic is termed the nonrecurrent or donor parent. This terminology refers to the fact that the nonrecurrent parent is used one time in the backcross protocol and therefore does not recur. The parental honeydew melon plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated 1, 2, 3, 4, 5, 6, 7, 8, 9 or more times until a honeydew melon plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility (such as a PR glucanase gene), herbicide resistance, resistance for bacterial, fungal (genes Fom-1 and Fom-2 for resistance to *Fusarium* wilt), or viral disease (gene nvs for resistance to melon necrotic spot virus), insect resistance (gene Vat for resistance to *Aphis gossypii*), male fertility, enhanced nutritional quality, enhanced sugar content, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tables

In the following tables, honeydew melon hybrids SSC 112, SSC 134, SSC 135 and SSC 118 and inbreds 10217-3, 10233-1, 11466, 11647, 10888, 10288-1 and 11876-1 are compared to each other and to commercial honeydew melon cultivars for the characteristics of fruit flesh firmness (Firmness) and percent soluble solids (% Soluble Solids). The fruit flesh firmness means the pound-force required to insert a 7 mm diameter probe to a depth of 7 mm at a point midway between the fruit rind and the seed cavity. "Percent soluble solids" means the percent of soluble solid material found in the fruit tissue, the vast majority of which consists of sugars. Soluble solids are estimated with a refractometer and measured as degrees Brix. The average firmness and the average percent soluble solids for five mature fruit each are reported below.

TABLE 12

2003 Location 1 Trial Results - Huron, CA

| Variety | Days to Maturity | Firmness | % Soluble Solids |
|---|---|---|---|
| SSC 112 | 105 | 8.100 | 14.32 |
| Santa Fe | 103 | 6.000 | 11.72 |

TABLE 12-continued

2003 Location 1 Trial Results - Huron, CA

| Variety | Days to Maturity | Firmness | % Soluble Solids |
|---|---|---|---|
| Vanessa | 99 | 5.100 | 12.92 |
| Haley | 103 | 5.675 | 11.32 |

TABLE 13

2003 Location 2 Trial Results - Wenden, AZ

| Variety | Days to Maturity | Firmness | % Soluble Solids |
|---|---|---|---|
| SSC 112 | 80 | 8.050 | 14.24 |
| Emerald | 84 | 6.575 | 11.16 |
| Verde | 84 | 5.900 | 11.84 |
| Vanessa | 72 | 4.975 | 11.16 |
| Haley | 75 | 5.150 | 12.12 |
| Sophia | 77 | 5.050 | 12.96 |
| Caroline | 77 | 5.375 | 11.44 |

TABLE 14

2003 Location 3 Trial Results - Mendota, CA

| Variety | Days to Maturity | Firmness | % Soluble Solids |
|---|---|---|---|
| SSC 112 | 92 | 8.550 | 14.52 |
| Emerald | 95 | 7.200 | 12.08 |
| Verde | 95 | 6.525 | 12.44 |
| Vanessa | 84 | 4.525 | 13.40 |
| Haley | 88 | 4.900 | 11.88 |
| Sophia | 88 | 4.950 | 12.96 |
| Caroline | 88 | 5.225 | 11.08 |

TABLE 15

2003 Location 4 Trial Results - Mendota, CA

| Variety | Days to Maturity | Firmness | % Soluble Solids |
|---|---|---|---|
| SSC 112 | 92 | 8.375 | 16.28 |
| 10217-3 | 94 | 6.550 | 17.16 |
| 10233-1 | 87 | 9.025 | 13.64 |
| SSC 118 | 90 | 5.775 | 13.64 |
| Sophia | 87 | 4.750 | 14.12 |
| Saturno | 87 | 5.700 | 13.52 |
| Verde | 94 | 6.725 | 12.64 |
| Emerald | 94 | 6.775 | 12.36 |
| Vanessa | 87 | 5.575 | 14.56 |
| Haley | 90 | 5.075 | 13.44 |
| Caroline | 90 | 5.500 | 12.56 |

TABLE 16

2003 Location 5 Trial Results - Mendota, CA

| Variety | Days to Maturity | Firmness | % Soluble Solids |
|---|---|---|---|
| SSC 112 | 86 | 9.025 | 14.44 |
| SSC 118 | 82 | 5.400 | 15.36 |
| Emerald | 89 | 7.150 | 12.04 |
| Verde | 89 | 6.725 | 12.52 |
| Vanessa | 80 | 5.100 | 13.32 |
| Haley | 82 | 5.500 | 11.72 |
| Sophia | 82 | 4.900 | 13.76 |
| Caroline | 84 | 4.725 | 12.60 |

TABLE 17

2003 Location 6 Trial Results - Wenden, AZ

| Variety | Days to Maturity | Firmness | % Soluble Solids |
|---|---|---|---|
| SSC 112 | 84 | 8.725 | 14.04 |
| SSC 118 | 80 | 5.725 | 14.36 |
| Emerald | 86 | 7.075 | 11.12 |
| HD Green Flesh | 86 | 6.825 | 10.68 |
| Verde | 86 | 6.525 | 12.68 |
| Vanessa | 78 | 4.625 | 13.50 |
| Haley | 80 | 5.775 | 12.84 |
| Sophia | 78 | 4.900 | 13.88 |
| Caroline | 82 | 5.750 | 11.80 |

TABLE 18

2004 Location 7 Trial Results - Nayarit, Mexico

| Variety | Days to Maturity From Transplant | Firmness | % Soluble Solids |
|---|---|---|---|
| SSC 112 | 72 | 8.750 | 15.04 |
| SSC 118 | 70 | 5.975 | 13.76 |
| Honey Comb | 72 | 5.500 | 12.36 |
| Verde | 77 | 7.025 | 11.60 |
| Emerald | 77 | 7.250 | 11.80 |
| Vanessa | 67 | 5.025 | 13.64 |
| Haley | 70 | 5.750 | 13.04 |
| Sophia | 69 | 5.775 | 12.64 |
| Caroline | 70 | 5.725 | 12.64 |

TABLE 19

2004 Location 8 Trial Results - Zacapa, Guatemala

| Variety | Days to Maturity From Transplant | Firmness | % Soluble Solids |
|---|---|---|---|
| SSC 112 | 62 | 9.025 | 14.44 |
| SSC 118 | 62 | 5.050 | 12.84 |
| Perla de Oriente | 62 | 6.040 | 10.64 |
| Verde | 65 | 6.525 | 13.00 |
| Emerald | 65 | 7.000 | 11.04 |
| Vanessa | 59 | 4.875 | 12.08 |
| Haley | 62 | 5.200 | 10.28 |
| Sophia | 60 | 5.525 | 10.84 |
| Caroline | 62 | 5.325 | 10.56 |

TABLE 20

2004 Location 9 Trial Results - Rio Grande City, TX

| Variety | Days to Maturity | Firmness | % Soluble Solids |
|---|---|---|---|
| SSC 112 | 90 | 8.600 | 15.24 |
| SSC 118 | 86 | 5.775 | 12.64 |
| Honeybrew | 90 | 5.275 | 11.04 |
| Morning Ice | 90 | 5.800 | 10.52 |
| Emerald | 93 | 6.500 | 11.08 |
| Vanessa | 85 | 4.775 | 13.96 |
| Haley | 88 | 5.425 | 11.40 |
| Sophia | 86 | 5.275 | 11.00 |
| Caroline | 88 | 5.400 | 11.48 |

TABLE 21

2004 Location 10 Trial Results - Harquahela, AZ

| Variety | Days to Maturity | Firmness | % Soluble Solids |
|---|---|---|---|
| SSC 112 | 102 | 8.375 | 14.80 |
| SSC 118 | 100 | 5.575 | 13.20 |
| Santa Fe | 100 | 5.275 | 12.44 |
| Verde | 105 | 6.025 | 11.64 |
| Emerald | 105 | 6.725 | 11.04 |
| Vanessa | 97 | 5.000 | 13.04 |
| Haley | 100 | 5.275 | 12.60 |
| Sophia | 97 | 5.225 | 12.76 |
| Caroline | 100 | 5.225 | 12.08 |

TABLE 22

2004 Location 11 Trial Results - Wenden, AZ

| Variety | Days to Maturity | Firmness | % Soluble Solids |
|---|---|---|---|
| SSC 112 | 81 | 8.275 | 15.84 |
| SSC 118 | 78 | 6.200 | 14.36 |
| Santa Fe | 78 | 6.000 | 14.00 |
| Sweet Delight | 86 | 6.825 | 13.36 |
| Honey Ace | 75 | 5.600 | 13.88 |
| Verde | 88 | 6.975 | 13.80 |
| Emerald | 88 | 7.125 | 13.40 |
| Vanessa | 75 | 5.750 | 14.24 |
| Haley | 78 | 6.225 | 14.20 |
| Sophia | 76 | 6.100 | 13.76 |
| Caroline | 78 | 6.050 | 13.24 |

TABLE 23

2004 Location 12 Trial Results - Coalinga, CA

| Variety | Days to Maturity | Firmness | % Soluble Solids |
|---|---|---|---|
| SSC 112 | 88 | 8.000 | 14.12 |
| SSC 118 | 86 | 5.000 | 14.28 |
| Verde | 90 | 6.750 | 12.56 |
| Saturno | 86 | 4.825 | 13.40 |
| Emerald | 90 | 6.775 | 12.40 |
| Vanessa | 84 | 4.525 | 14.00 |
| Haley | 86 | 5.025 | 11.64 |
| Sophia | 84 | 4.775 | 13.56 |
| Caroline | 86 | 5.250 | 10.84 |

TABLE 24

2004 Location 13 Trial Results - Mendota, CA

| Variety | Days to Maturity | Firmness | % Soluble Solids |
|---|---|---|---|
| SSC 112 | 90 | 8.050 | 15.24 |
| 10217-3 | 95 | 7.100 | 16.44 |
| 10233-1 | 87 | 8.750 | 14.36 |
| SSC 118 | 88 | 4.550 | 15.56 |
| Verde | 95 | 6.225 | 13.84 |
| Saturno | 82 | 4.625 | 14.92 |
| Emerald | 95 | 6.650 | 14.76 |
| Vanessa | 82 | 4.100 | 16.24 |
| Haley | 87 | 4.625 | 13.04 |
| Sophia | 85 | 4.450 | 14.80 |
| Caroline | 87 | 4.275 | 12.36 |

TABLE 25

2004 Location 14 Trial Results - Mendota, CA

| Variety | Days to Maturity | Firmness | % Soluble Solids |
|---|---|---|---|
| SSC 112 | 80 | 8.250 | 14.76 |
| 10217-3 | 82 | 6.550 | 16.00 |
| 10233-1 | 75 | 8.725 | 13.44 |
| SSC 118 | 80 | 5.525 | 14.40 |
| Verde | 85 | 6.975 | 12.04 |
| Emerald | 85 | 6.525 | 10.56 |
| Vanessa | 72 | 4.525 | 13.24 |
| Haley | 76 | 5.475 | 11.00 |
| Sophia | 75 | 5.225 | 11.24 |
| Caroline | 78 | 5.525 | 10.24 |

TABLE 26

2004 Location 15 Trial Results - Wenden, AZ

| Variety | Days to Maturity | Firmness | % Soluble Solids |
|---|---|---|---|
| SSC 112 | 69 | 9.500 | 13.60 |
| SSC 118 | 65 | 5.525 | 10.64 |
| Santa Fe | 65 | 4.525 | 11.96 |
| Honey Ace | 64 | 4.350 | 12.24 |
| Emerald | 74 | 7.475 | 10.76 |
| Haley | 66 | 4.525 | 11.00 |
| Sophia | 65 | 5.725 | 9.76 |
| Caroline | 67 | 5.050 | 10.44 |

TABLE 27

2004 Location 16 Trial Results - Wenden, AZ

| Variety | Days to Maturity | Firmness | % Soluble Solids |
|---|---|---|---|
| SSC 112 | 68 | 8.600 | 14.08 |
| Sweet Delight | 73 | 6.975 | 10.04 |
| Moonshine | 60 | 6.525 | 11.44 |

TABLE 28

2003 Location 17 Trial Results - Mendota, CA

| Variety | Days to Maturity | Firmness | % Soluble Solids |
|---|---|---|---|
| SSC 112 | 92 | 8.375 | 16.28 |
| 10217-3 | 94 | 6.550 | 17.16 |
| 10233-1 | 87 | 9.025 | 13.64 |
| 11466 | 92 | 10.475 | 12.44 |
| 11647 | 92 | 5.175 | 15.12 |
| SSC 118 | 90 | 5.775 | 13.64 |
| Sophia | 87 | 4.750 | 14.12 |
| Saturno | 87 | 5.700 | 13.52 |
| Verde | 94 | 6.725 | 12.64 |
| Emerald | 94 | 6.775 | 12.36 |
| Vanessa | 87 | 5.575 | 14.56 |
| Haley | 90 | 5.075 | 13.44 |
| Caroline | 90 | 5.500 | 12.56 |

TABLE 29

2004 Location 18 Trial Results - Harquahela, AZ

| Variety | Days to Maturity | Firmness | % Soluble Solids |
|---|---|---|---|
| SSC 112 | 102 | 8.375 | 14.80 |
| SSC 134 | 102 | 8.6 | 13.88 |
| SSC 118 | 100 | 5.575 | 13.20 |
| Santa Fe | 100 | 5.275 | 12.44 |
| Verde | 105 | 6.025 | 11.64 |
| Emerald | 105 | 6.725 | 11.04 |
| Vanessa | 97 | 5.000 | 13.04 |
| Haley | 100 | 5.275 | 12.60 |
| Sophia | 97 | 5.225 | 12.76 |
| Caroline | 100 | 5.225 | 12.08 |

TABLE 30

2004 Location 19 Trial Results - Mendota, CA

| Variety | Days to Maturity | Firmness | % Soluble Solids |
|---|---|---|---|
| SSC 112 | 90 | 8.050 | 15.24 |
| 10217-3 | 95 | 7.100 | 16.44 |
| 10233-1 | 87 | 8.750 | 14.36 |
| 11466 | 88 | 9.350 | 13.88 |
| 11647 | 90 | 4.525 | 15.28 |
| 11696 | 87 | 8.100 | 13.08 |
| SSC 134 | 90 | 8.000 | 14.28 |
| SSC 135 | 90 | 8.400 | 15.16 |
| SSC 118 | 88 | 4.550 | 15.56 |
| Verde | 95 | 6.225 | 13.84 |
| Saturno | 82 | 4.625 | 14.92 |
| Emerald | 95 | 6.650 | 14.76 |
| Vanessa | 82 | 4.100 | 16.24 |
| Haley | 87 | 4.625 | 13.04 |
| Sophia | 85 | 4.450 | 14.80 |
| Caroline | 87 | 4.275 | 12.36 |

TABLE 31

2004 Location 20 Trial Results - Mendota, CA

| Variety | Days to Maturity | Firmness | % Soluble Solids |
|---|---|---|---|
| SSC 112 | 80 | 8.250 | 14.76 |
| 10217-3 | 82 | 6.550 | 16.00 |
| 10233-1 | 75 | 8.725 | 13.44 |
| SSC 134 | 78 | 7.850 | 15.32 |
| SSC 118 | 80 | 5.525 | 14.40 |
| Verde | 85 | 6.975 | 12.04 |
| Emerald | 85 | 6.525 | 10.56 |
| Vanessa | 72 | 4.525 | 13.24 |
| Haley | 76 | 5.475 | 11.00 |
| Sophia | 75 | 5.225 | 11.24 |
| Caroline | 78 | 5.525 | 10.24 |

TABLE 32

2004 Location 21 Trial Results - Wenden, AZ

| Variety | Days to Maturity | Firmness | % Soluble Solids |
|---|---|---|---|
| SSC 112 | 69 | 9.500 | 13.60 |
| SSC 134 | 71 | 9.300 | 14.16 |
| SSC 135 | 71 | 9.600 | 12.84 |
| SSC 118 | 65 | 5.525 | 10.64 |
| Santa Fe | 65 | 4.525 | 11.96 |
| Honey Ace | 64 | 4.350 | 12.24 |
| Emerald | 74 | 7.475 | 10.76 |

TABLE 32-continued

2004 Location 21 Trial Results - Wenden, AZ

| Variety | Days to Maturity | Firmness | % Soluble Solids |
|---|---|---|---|
| Haley | 66 | 4.525 | 11.00 |
| Sophia | 65 | 5.725 | 9.76 |
| Caroline | 67 | 5.050 | 10.44 |

TABLE 33

2003 Location 22 Trial Results - Mendota, CA

| Variety | Days to Maturity | Firmness | % Soluble Solids |
|---|---|---|---|
| SSC 112 | 92 | 8.375 | 16.28 |
| 10217-3 | 94 | 6.550 | 17.16 |
| 10233-1 | 87 | 9.025 | 13.64 |
| 11466 | 92 | 10.475 | 12.44 |
| 11647 | 92 | 5.175 | 15.12 |
| 10888 | 87 | 4.500 | 15.00 |
| 10228-1 | 90 | 6.375 | 12.28 |
| SSC 118 | 90 | 5.775 | 13.64 |
| Sophia | 87 | 4.750 | 14.12 |
| Saturno | 87 | 5.700 | 13.52 |
| Verde | 94 | 6.725 | 12.64 |
| Emerald | 94 | 6.775 | 12.36 |
| Vanessa | 87 | 5.575 | 14.56 |
| Haley | 90 | 5.075 | 13.44 |
| Caroline | 90 | 5.500 | 12.56 |

TABLE 34

2004 Location 23 Trial Results - Mendota, CA

| Variety | Days to Maturity | Firmness | % Soluble Solids |
|---|---|---|---|
| SSC 112 | 90 | 8.050 | 15.24 |
| 10217-3 | 95 | 7.100 | 16.44 |
| 10233-1 | 87 | 8.750 | 14.36 |
| 11466 | 88 | 9.350 | 13.88 |
| 11647 | 90 | 4.525 | 15.28 |
| 11696 | 87 | 8.100 | 13.08 |
| 10888 | 85 | 4.100 | 15.36 |
| 10228-1 | 90 | 7.100 | 12.84 |
| SSC 134 | 90 | 8.000 | 14.28 |
| SSC 135 | 90 | 8.400 | 15.16 |
| SSC 118 | 88 | 4.550 | 15.56 |
| Verde | 95 | 6.225 | 13.84 |
| Saturno | 82 | 4.625 | 14.92 |
| Emerald | 95 | 6.650 | 14.76 |
| Vanessa | 82 | 4.100 | 16.24 |
| Haley | 87 | 4.625 | 13.04 |
| Sophia | 85 | 4.450 | 14.80 |
| Caroline | 87 | 4.275 | 12.36 |

DEPOSIT INFORMATION

Deposits of the Shamrock Seed Company, Inc. proprietary Melon Cultivars 10217-3, 11466, 10888, 11876-1, 10233-1, SSC 112, SSC 135, 10228-1, SSC 118 disclosed above and recited in the appended claims has been made with the American Type Culture Collection (ATCC), 10801 University Boulevard, Manassas, Va. 20110. The date of deposits was Nov. 4, 2008. The deposits of 2,500 seeds were taken from the same deposits maintained by Shamrock Seed Company, Inc. since prior to the filing date of this application. All restrictions will be irrevocably removed upon granting of a patent, and the deposits are intended to meet all of the requirements of 37 C.F.R. §§1.801-1.809. The ATCC Accession Numbers are PTA-9573, 9574, 9575, 9576, 9577, 9578, 9579, 9580, and 9581, respectively. The deposits will be maintained in the depository for a period of thirty years, or five years after the last request, or for the enforceable life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant line and the like may be practiced within the scope of the invention, as limited only by the scope of the appended claims.

What is claimed is:

1. A method of selecting for a hybrid melon plant that produces a hybrid honeydew melon fruit having both a percent soluble solids of 13.5% to 17.3% and a flesh firmness of 6.8 to 10.7, wherein the method comprises:
   (a) crossing a first inbred honeydew melon parent plant having fruit with both a percent soluble solids of 12.28% to 17.16% and a flesh firmness of 4.1 to 10.475 with a second inbred honeydew melon plant having fruit with both a percent soluble solids of 12.28% to 17.16% and a flesh firmness of 4.1 to 10.475;
   (b) harvesting the resultant hybrid honeydew melon seed;
   (c) growing said hybrid honeydew melon seed; and
   (d) selecting a hybrid melon plant that produces a hybrid honeydew melon fruit with both a percent soluble solids of 13.5% to 17.3% and a flesh firmness of 6.8 to 10.7.

2. The method of claim 1, wherein the first parent plant or the second parent plant is selected from the group consisting of inbred melon cultivars 10217-3, 11466, 10888, 11876-1, 10233-1, and 10228-1, wherein representative seed of said cultivars has been deposited under ATCC Deposit Nos. PTA-9573, PTA-9574, PTA-9575, PTA-9576, PTA-9577 and PTA-9580, respectively.

3. The method of claim 2, wherein the first parent plant or the second parent plant is selected from the group consisting of inbred melon cultivars 10217-3, 11466, and 10233-1.

4. The method of claim 1, wherein the hybrid melon plant is selected to produce hybrid honeydew melon fruit with percent soluble solids of 14.7% to 16.5%.

5. The method of claim 1, wherein the hybrid melon plant is selected to produce hybrid honeydew melon fruit with flesh firmness of 6.8 to 8.5.

6. The method of claim 1, wherein the hybrid melon plant is selected to produce hybrid honeydew melon fruit with percent soluble solids of 16.5% to 17.3%.

7. The method of claim 1, wherein the hybrid melon plant is selected to produce hybrid honeydew melon fruit with flesh firmness of 8.5 to 10.7.

8. A method of producing an herbicide resistant hybrid honeydew melon plant, wherein the method comprises transforming the hybrid honeydew melon plant selected in claim 1 with a transgene, wherein said transgene confers resistance to an herbicide selected from the group consisting of imidazolinone, sulfonylurea, glyphosate, glufosinate, L-phosphinothricin, triazine and benzonitrile.

9. The method of claim 8, wherein the transgene confers resistance to imidazolinone herbicides.

10. A method of producing an insect resistant hybrid honeydew melon plant, wherein the method comprises transforming the hybrid honeydew melon plant selected in claim 1 with a transgene that confers insect resistance.

11. The method of claim 10, wherein the transgene encodes a *Bacillus thuringiensis* endotoxin.

12. A method of producing a disease resistant hybrid honeydew melon plant, wherein the method comprises transforming the honeydew melon plant selected in claim 1 with a transgene that confers disease resistance.

13. A method of introducing a desired trait into the hybrid honeydew melon plant selected in claim 1, wherein the method comprises:

(a) crossing the plant selected in claim 1 with a plant of another honeydew melon cultivar that comprises a desired trait to produce progeny plants, wherein the desired trait is selected from the group consisting of male sterility, herbicide resistance, insect resistance, and resistance to bacterial disease, fungal disease and viral disease;

(b) selecting progeny plants that have the desired trait;

(c) backcrossing said selected progeny plants with the plant selected in claim 1;

(d) selecting for backcross progeny plants that have the desired trait; and (e) repeating steps (c) and (d) two or more times in succession to produce selected second or higher backcross progeny plants that comprise the desired trait.

* * * * *